(12) United States Patent
Seiger et al.

(10) Patent No.: US 9,072,506 B1
(45) Date of Patent: Jul. 7, 2015

(54) BIOPSY APPARATUS INCLUDING A BIOPSY DEVICE HAVING A SAMPLE RECEIVING NOTCH WITH A TISSUE ANCHOR

(75) Inventors: Jason G. Seiger, Gilbert, AZ (US); Rafal Chudzik, Peoria, AZ (US); Angela K. Jensen, Mesa, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 525 days.

(21) Appl. No.: 12/552,475

(22) Filed: Sep. 2, 2009

(51) Int. Cl.
*A61B 10/02* (2006.01)
*A61B 17/32* (2006.01)

(52) U.S. Cl.
CPC ......... *A61B 10/0275* (2013.01); *A61B 10/0283* (2013.01)

(58) Field of Classification Search
USPC .................. 600/564–567, 568; 606/167, 170
See application file for complete search history.

(56) References Cited

U.S. PATENT DOCUMENTS

| | | |
|---|---|---|
| 3,800,783 A | 4/1974 | Jamshidi |
| 3,844,272 A | 10/1974 | Banko |
| 3,929,123 A | 12/1975 | Jamshidi |
| 4,517,965 A | 5/1985 | Ellison |
| 4,874,375 A | 10/1989 | Ellison |
| RE33,258 E | 7/1990 | Onik et al. |
| 5,031,634 A | 7/1991 | Simon |
| 5,320,110 A | 6/1994 | Wang |
| 5,335,671 A | 8/1994 | Clement |
| 5,526,822 A | 6/1996 | Burbank et al. |
| 5,601,585 A | 2/1997 | Banik et al. |
| 5,649,939 A | 7/1997 | Reddick |
| 5,769,086 A | 6/1998 | Ritchart et al. |
| 5,830,219 A | 11/1998 | Bird et al. |
| 5,879,365 A | 3/1999 | Whitfield et al. |
| 5,928,164 A | 7/1999 | Burbank et al. |
| 6,086,544 A | 7/2000 | Hibner et al. |
| 6,093,154 A | 7/2000 | Burek et al. |
| 6,120,462 A | 9/2000 | Hibner et al. |
| 6,273,862 B1 | 8/2001 | Privitera et al. |
| 6,331,166 B1 | 12/2001 | Burbank et al. |
| 6,428,487 B1 | 8/2002 | Burdorff et al. |
| 6,585,664 B2 | 7/2003 | Burdorff et al. |
| 6,659,105 B2 | 12/2003 | Burbank et al. |
| 6,709,408 B2 | 3/2004 | Fisher |
| 6,712,773 B1 * | 3/2004 | Viola .............................. 600/564 |
| 6,752,768 B2 | 6/2004 | Burdorff et al. |
| 6,872,185 B2 | 3/2005 | Fisher |
| 6,890,309 B2 | 5/2005 | Fisher |
| 7,147,607 B2 | 12/2006 | Wang |

(Continued)

FOREIGN PATENT DOCUMENTS

GB        2018601 A        10/1979

*Primary Examiner* — Lee S Cohen
*Assistant Examiner* — Emily Lloyd

(57) ABSTRACT

A biopsy device includes a sample receiving notch formed in an elongate member. The sample receiving notch defines a side port adjacent the outer surface. The sample receiving notch extends inwardly from the side port toward a longitudinal axis and terminates at a sample floor in an interior of the elongate member. The sample receiving notch has a proximal end wall separated from a distal end wall along the longitudinal axis. The floor extends between the proximal end wall and the distal end wall. A tissue anchor has a cantilever portion and a head portion at a free end of the cantilever portion. The cantilever portion extends from a distal portion of the elongate member adjacent to the sample receiving notch toward the proximal end wall of the sample receiving notch. The head portion has a sharp tip that extends from the cantilever portion toward the sample floor.

18 Claims, 6 Drawing Sheets

(56) References Cited

U.S. PATENT DOCUMENTS

| | | |
|---|---|---|
| 7,153,274 B2 | 12/2006 | Stephens et al. |
| 7,189,206 B2 | 3/2007 | Quick et al. |
| 7,226,424 B2 | 6/2007 | Ritchart et al. |
| 7,347,829 B2 | 3/2008 | Mark et al. |
| 7,648,466 B2 | 1/2010 | Stephens et al. |
| 7,717,930 B2 * | 5/2010 | Paul et al. .................... 606/167 |
| 2004/0267157 A1 | 12/2004 | Miller et al. |
| 2005/0113716 A1 | 5/2005 | Mueller, Jr. et al. |
| 2008/0154151 A1 | 6/2008 | Ritchart et al. |
| 2008/0208194 A1 | 8/2008 | Bickenbach |

* cited by examiner

BIOPSY APPARATUS INCLUDING A BIOPSY DEVICE HAVING A SAMPLE RECEIVING NOTCH WITH A TISSUE ANCHOR

CROSS-REFERENCE TO RELATED APPLICATIONS

None.

MICROFICHE APPENDIX

None.

GOVERNMENT RIGHTS IN PATENT

None.

BACKGROUND OF THE INVENTION

1. Field of the Invention

The present invention relates to a biopsy apparatus, and, more particularly, to a biopsy apparatus including a biopsy device having a sample receiving notch with a tissue anchor.

2. Description of the Related Art

A biopsy may be performed on a patient to help in determining whether the cells in a biopsied region are cancerous. One biopsy technique used to evaluate breast tissue, for example, involves inserting a biopsy probe into the breast tissue region of interest to capture one or more tissue samples from the region. Such a biopsy technique often utilizes a vacuum to pull the tissue to be sampled into a sample receiving notch of the biopsy probe, after which the tissue is severed and collected. One type of vacuum assisted biopsy apparatus includes a hand-held driver assembly having a pressure source, and a disposable biopsy probe assembly configured for releasable attachment to the driver assembly. The biopsy probe typically includes a biopsy cannula, e.g., a needle, having a side sample port for receiving the tissue to be sampled.

U.S. Pat. No. 3,929,123 discloses various embodiments of a biopsy needle configured as a shaft having a sample retaining cavity, and barbs in the sample chamber to engage tissue coming into the confines of the sample retaining cavity. However, with such a barb hook arrangement, when cut by an external cutter the sample may be forced to the distal end of the sample chamber, potentially damaging the tissue sample by the barbs. Further, such barbs may make tissue release difficult.

SUMMARY OF THE INVENTION

The present invention provides a biopsy apparatus configured to collect a tissue sample of increased size and/or quality over that which may be otherwise obtained in the absence of the invention.

The invention, in one form thereof, is directed to a biopsy device. The biopsy device includes an elongate member having a proximal end, a distal end, an outer surface, and a longitudinal axis extending between the proximal end and the distal end. A sample receiving notch is formed in the elongate member. The sample receiving notch defines a side port adjacent the outer surface. The sample receiving notch extends inwardly from the side port toward the longitudinal axis and terminates at a sample floor in an interior of the elongate member. The sample receiving notch has a proximal end wall and a distal end wall. The proximal end wall is separated from the distal end wall along the longitudinal axis. The floor extends between the proximal end wall and the distal end wall along the longitudinal axis. A tissue anchor has a cantilever portion and a head portion at a free end of the cantilever portion. The cantilever portion extends from a distal portion of the elongate member adjacent to the sample receiving notch toward the proximal end wall of the sample receiving notch. The head portion has a sharp tip that extends from the cantilever portion toward the sample floor.

The invention, in another form thereof, is directed to a biopsy probe mechanism. The biopsy probe mechanism includes a frame, a cutting cannula, and an elongate member. The elongate member is arranged coaxially with the cutting cannula. The cutting cannula and the elongate member are coupled to the frame. The elongate member has a proximal end, a distal end, an outer surface, and a longitudinal axis extending between the proximal end and the distal end. A lumen is formed in the elongate member, the lumen beginning at the proximal end and extending toward the distal end along the longitudinal axis. A sample receiving notch is formed in the elongate member. The sample receiving notch defines a side port adjacent the outer surface. The sample receiving notch extends inwardly from the side port toward the longitudinal axis and terminates at a sample floor in an interior of the elongate member. The sample receiving notch has a proximal end wall and a distal end wall. The proximal end wall is separated from the distal end wall along the longitudinal axis. The floor extends between the proximal end wall and the distal end wall along the longitudinal axis. The proximal end wall has a hole that facilitates fluid communication between the sample receiving notch and the lumen. A tissue anchor has a cantilever portion and a head portion at a free end of the cantilever portion. The cantilever portion extends from a distal portion of the elongate member adjacent to the sample receiving notch toward the proximal end wall of the sample receiving notch. The head portion has a sharp tip that extends from the cantilever portion toward the sample floor.

The invention, in another form thereof, is directed to a biopsy apparatus. The biopsy apparatus includes a driver assembly having a housing configured to be grasped by a user, a pressure source, and a biopsy probe mechanism. The biopsy probe mechanism is drivably coupled to the driver assembly. The biopsy probe mechanism includes a cutting cannula and an elongate member. The elongate member is arranged coaxially with the cutting cannula. The elongate member has a proximal end, a distal end, an outer surface, and a longitudinal axis extending between the proximal end and the distal end. A lumen is formed in the elongate member, the lumen beginning at the proximal end and extending toward the distal end along the longitudinal axis. The lumen is connected in fluid communication with the pressure source. A sample receiving notch is formed in the elongate member. The sample receiving notch defines a side port adjacent the outer surface. The sample receiving notch extends inwardly from the side port toward the longitudinal axis and terminates at a sample floor in an interior of the elongate member. The sample receiving notch has a proximal end wall and a distal end wall. The proximal end wall is separated from the distal end wall along the longitudinal axis. The floor extends between the proximal end wall and the distal end wall along the longitudinal axis. The proximal end wall has a hole that facilitates fluid communication between the sample receiving notch and the lumen. A tissue anchor has a cantilever portion and a head portion at a free end of the cantilever portion. The cantilever portion extends from a distal portion of the elongate member adjacent to the sample receiving notch toward the proximal end wall of the sample receiving notch. The head portion has a sharp tip that extends from the cantilever portion toward the sample floor.

The invention, in another form thereof, is directed to a method for performing a biopsy procedure with a biopsy apparatus having a biopsy probe mechanism, the biopsy probe mechanism having a cutting cannula and a sample receiving notch in fluid communication with a pressure source. The method includes inserting a distal portion of the biopsy probe mechanism into tissue of a patient with the sample receiving notch covered by the cutting cannula; moving the cutting cannula relative to the sample receiving notch to expose the sample receiving notch to receive a tissue portion of the tissue; securing a distal end portion of the tissue portion received in the sample receiving notch to a tissue anchor of the biopsy probe mechanism; pulling a proximal end portion of the tissue portion received in the sample receiving notch away from the distal end portion to place the tissue portion received in the sample receiving notch in a state of tension across the sample receiving notch; and covering the sample receiving notch with the cutting cannula to sever the tissue portion to collect a tissue sample of the tissue of the patient while the tissue portion received in the sample receiving notch is in the state of tension.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION OF THE INVENTION

Figure 1:
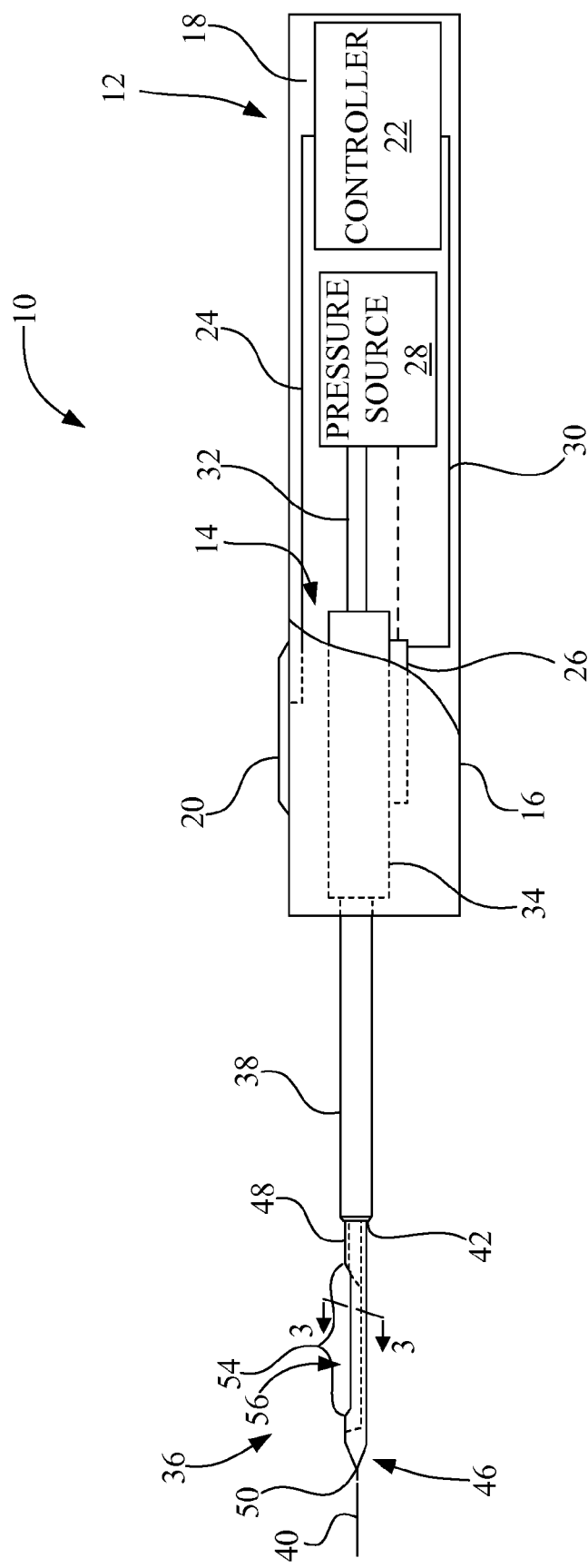
FIG. 1 is a side view of a biopsy apparatus configured in accordance with an embodiment of the present invention, with a biopsy probe mechanism mounted to a driver assembly, and with a side portion broken away to expose internal components which are schematically represented in part.

Referring now to the drawings, and more particularly to FIG. 1, there is shown a biopsy apparatus 10 which generally includes a driver assembly 12 and a biopsy probe mechanism 14.

Driver assembly 12 is configured to provide operative control over biopsy probe mechanism 14. Driver assembly 12 may be, for example, a non-disposable device, or alternatively a disposable device. As used herein, the term "non-disposable" is used to refer to a device that is intended for use on multiple patients during the lifetime of the device. Also, as used herein, the term "disposable" is used to refer to a device that is intended to be disposed of after use on a single patient.

Accordingly, in some embodiments driver assembly 12 and biopsy probe mechanism 14 may be releasably attached to one another. In other embodiments, however, it is contemplated that driver assembly 12 and biopsy probe mechanism 14 may be permanently attached to each other to form an integral biopsy apparatus, such that the entire biopsy apparatus is made to be disposable.

Driver assembly 12 includes a housing 16 configured, e.g., ergonomically designed, to be grasped by a user, e.g., a physician. Housing 16 defines a compartment 18 into which biopsy probe mechanism 14 is at least partially positioned when biopsy probe mechanism 14 is attached to driver assembly 12, with biopsy probe mechanism 14 being drivably coupled to driver assembly 12.

Driver assembly 12 further includes a user interface 20 located to be externally accessible to the user with respect to housing 16 for receiving operation commands from the user, e.g., through one or more pushbuttons, and may also include a display, e.g., one or more lights or an LCD (liquid crystal display), to display information to the user. A controller 22 is communicatively coupled user interface 20 via a communication link 24, such as for example, wire cabling, printed circuits, etc. Controller 22 may include, for example, a microprocessor and associated memory (not shown) for executing program instructions to perform functions associated with the harvesting of biopsy tissue samples during a biopsy procedure.

There is contained within housing 16 an electromechanical drive 26 and a pressure source 28. Electromechanical drive 26 is connected in electrical communication with controller 22 via a communication link 30, such as for example, wire cabling, printed circuits, etc. Electromechanical drive 26 is further drivably coupled (illustrated by dashed lines) to the biopsy probe mechanism 14 and to the pressure source 28 to selectively and operatively control biopsy probe mechanism 14 and pressure source 28. Electromechanical drive 26 may include, for example, one or more of a linear drive that converts rotational motion to linear motion (e.g., a worm gear arrangement, rack and pinion arrangement, solenoid-slide arrangement, etc.) and a rotational drive that may include one or more of a gear, gear train, belt/pulley arrangement, etc., for effecting operation of biopsy probe mechanism 14 and/or pressure source 28.

Pressure source 28 may be, for example, a peristaltic pump, a diaphragm pump, syringe-type pump, etc. Pressure source 28 may be permanently integrated into driver assembly 12, or alternatively may be permanently integrated as a part of the biopsy probe mechanism 14. In either case, pressure source 28 is coupled in fluid communication with biopsy probe mechanism 14, e.g., via conduit 32, and is configured to generate negative pressure (vacuum), and in some embodiments may also generate positive pressure.

Biopsy probe mechanism 14 is generally intended to be disposable as a unit. In the present embodiment, biopsy probe mechanism 14 is configured for one of permanent attachment or releasable attachment to driver assembly 12. As used herein, the term "releasable attachment" means a configuration that facilitates an intended temporary connection followed by selective detachment involving a manipulation of disposable biopsy probe mechanism 14 relative to driver assembly 12, e.g., without the need for tools.

Biopsy probe mechanism 14 includes a frame 34, an elongate member (e.g., a biopsy device) 36 and a cutting cannula 38. Elongate member 36 and a cutting cannula 38 are arranged coaxially with respect to a longitudinal axis 40. Cutting cannula 38 has a distal cutting edge 42. Elongate member 36 and a cutting cannula 38 are mounted as a coaxial unit to frame 34.

The operation of cutting cannula 38 of biopsy probe mechanism 14 may be brought about, for example, by controller 22 and electromechanical drive 26 via one or more of the linear drive that converts rotational motion to linear motion and the rotational drive. Thus, cutting cannula 38 may be controlled to translate linearly along longitudinal axis 40, and may further be controlled to cause cutting cannula 38 to rotate or oscillate about longitudinal axis 40 during the linear advancement, or to rotate or oscillate independent of any linear advancement.

Figure 2:
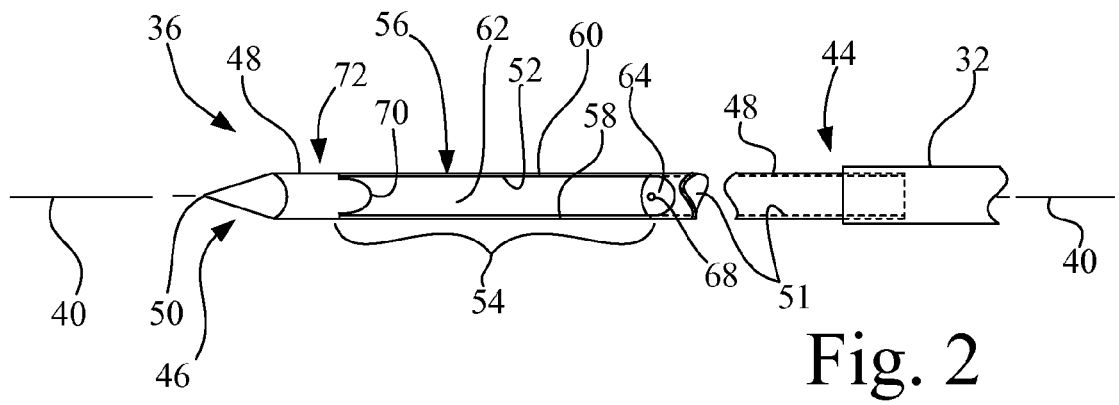
FIG. 2 is an enlarged top view of an elongate member of a portion of the biopsy probe mechanism of FIG. 1.
Figure 3:
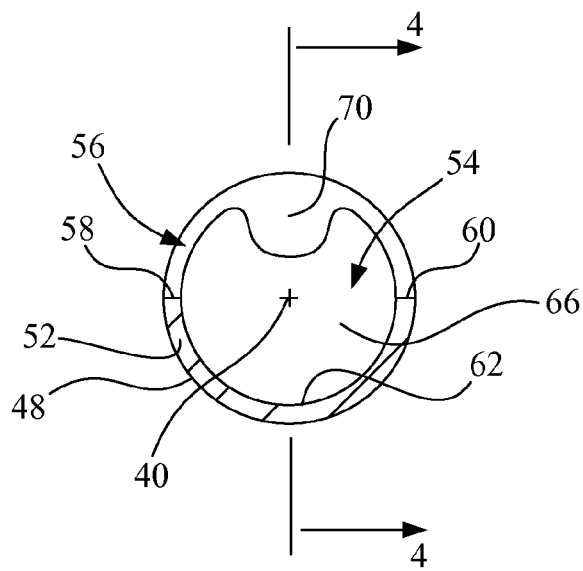
FIG. 3 is an enlarged section view of the elongate member of the biopsy probe mechanism of FIG. 1, taken along line 3-3 of FIG. 1.
Figure 4:
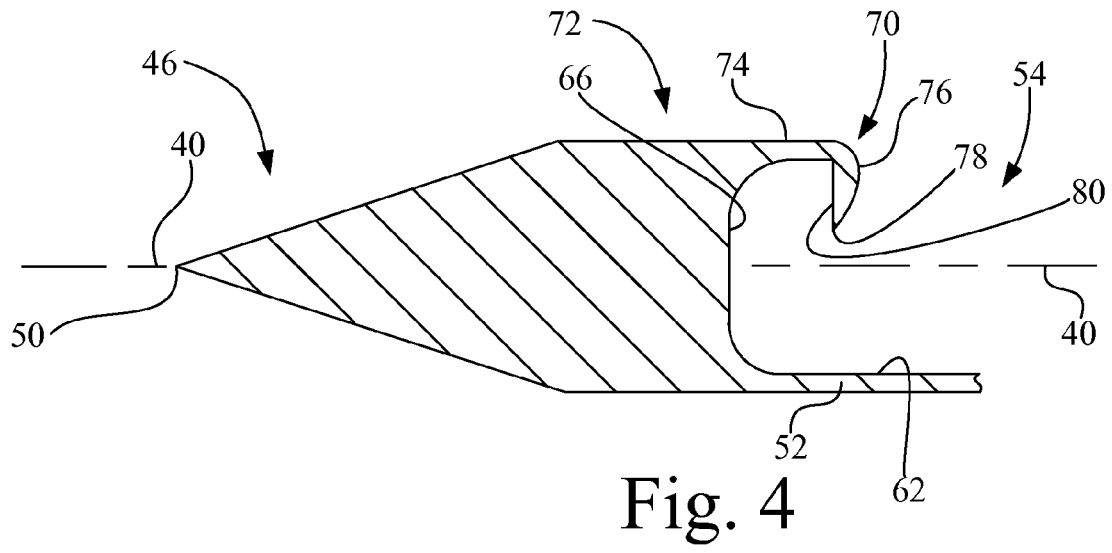
FIG. 4 is an enlarged section view of the elongate member taken along line 4-4 of FIG. 3.

Referring also to FIGS. 2-4, elongate member 36 has a proximal end 44, a distal end 46, and an outer surface 48. Elongate member 36 may be made, for example, from a metal, such as stainless steel, titanium, or a nickel alloy. In the present embodiment, distal end 46 has a piercing tip 50. Elongate member 36 may be formed, for example, from a cylindrical tube having a side wall 52, such as for example a biopsy cannula in the form of a hollow needle. Alternatively, elongate member may be formed from a solid rod. Longitudinal axis 40 extends between proximal end 44 and distal end 46.

In the exemplary embodiments described herein, a lumen 51 is located in elongate member that begins at proximal end 44 and extends toward distal end 46 along longitudinal axis 40. In turn, lumen 51 of elongate member 36 is coupled in fluid communication with pressure source 28 via conduit 32. It is to be understood, however, that lumen 51 may be eliminated in designs that do not utilize a pressure source.

A sample receiving notch 54 is formed in elongate member 36, e.g., by machining elongate member 36. Sample receiving notch 54 is configured to receive the tissue to be biopsied, and to retain the tissue sample harvested from the tissue, during a biopsy procedure. Sample receiving notch 54 may be also sometimes referred to as a sample chamber.

Sample receiving notch 54 defines a side port 56 adjacent outer surface 48, with side port 56 defining elongate upper edges 58, 60 of sample receiving notch 54. Sample receiving notch 54 extends inwardly from side port 56 toward longitudinal axis 40 and terminates at a sample floor 62 in an interior of elongate member 36. In some embodiments, as shown in cross-section in FIG. 3, a portion of cylindrical side wall 52 extends between elongate upper edges 58, 60, forming sample floor 62 opposite to side port 56.

Referring to FIGS. 2 and 4, sample receiving notch 54 has a proximal end wall 64 and a distal end wall 66. Proximal end wall 64 is separated from distal end wall 66 along longitudinal axis 40, with sample floor 62 extending between proximal end wall 64 and distal end wall 66 along longitudinal axis 40. In the present embodiment, proximal end wall 64 has a hole 68 that facilitates fluid communication between sample receiving notch 54 and lumen 51. As such, negative pressure or positive pressure is communicated to sample receiving notch 54 from pressure source 28 via hole 68 in proximal end wall 64.

Referring to FIGS. 1-4, in accordance with an aspect of the present invention, a tissue anchor 70 extends from a distal portion 72 of elongate member 36 toward proximal end wall 64. More particularly, tissue anchor 70 has a cantilever portion 74 and a head portion 76 at a free end of cantilever portion 74. Cantilever portion 74 extends from the distal portion 72 of elongate member 36 adjacent to sample receiving notch 54 toward proximal end wall 64 of sample receiving notch 54. Tissue anchor 70 may be formed, for example, from a portion of elongate member 36, such as for example, from a portion of side wall 52.

Head portion 76 extends in a cantilevered manner (downwardly in the orientation as shown) from cantilever portion 74. More particularly, head portion 76 has a sharp tip 78 that extends from cantilever portion 74 downwardly in a cantilevered manner toward sample floor 62. Sharp tip 78 of head portion 76 may include a planar face 80, wherein the plane of planar face 80 is oriented substantially perpendicular to longitudinal axis 40 and sample floor 62.

Figure 5:
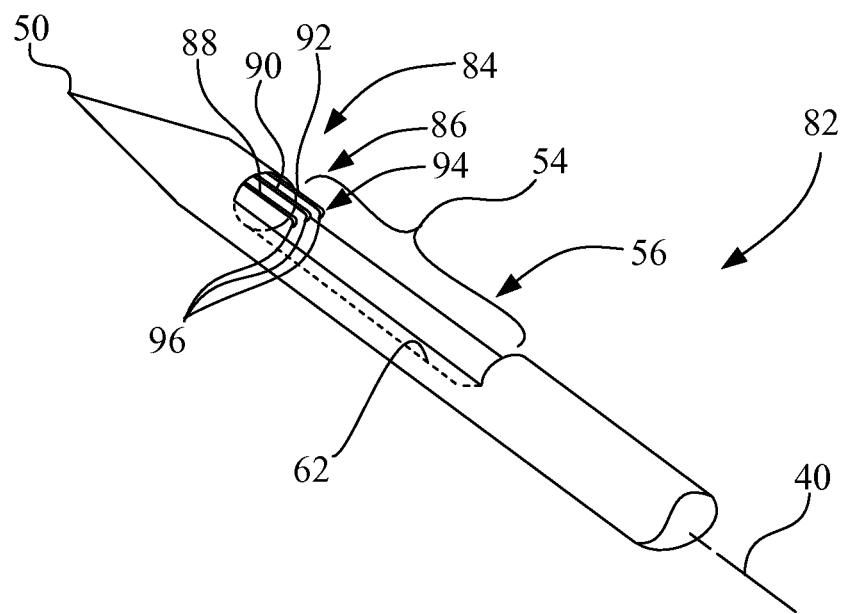
FIG. 5 is a perspective view of another embodiment of an elongate member suitable for use with the biopsy probe mechanism of FIG. 1.

FIG. 5 is a perspective view of another embodiment of an elongate member 82 suitable for use with the biopsy probe mechanism of FIG. 1, elongate member 82 is substantially identical to elongate member 36 described above, except for the configuration of the tissue anchor. Accordingly, for brevity, the subject matter common to both elongate member 36 and elongate member 82 will not be repeated here, and FIG. 5 will include element numbers common to both elongate member 36 and elongate member 82.

Figure 6:
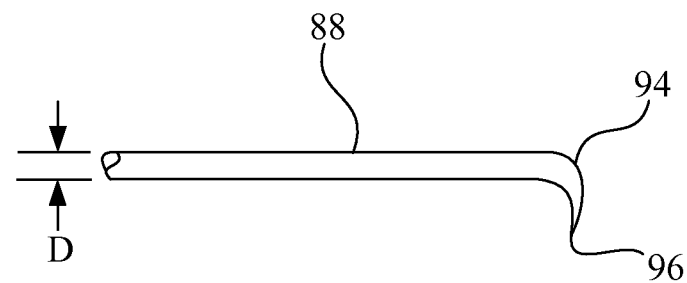
FIG. 6 is a side view of one of the cantilevered members used with the elongate member of FIG. 5.

Elongate member 82 includes a tissue anchor 84 that includes a plurality of cantilevered members 86, e.g., cantilevered members 88, 90 and 92 in the present example. Referring also to FIG. 6, each cantilevered member 88, 90, 92 of the plurality of cantilevered members 86 has a constant diameter D and a curved end 94, and with a tip end 96 of the curved end 94 extending toward sample floor 62. The tip ends 96 of the plurality of cantilevered members 86 engage tissue during a biopsy procedure, and tend to firmly hold a front portion of the tissue to be sampled.

Figure 7A:
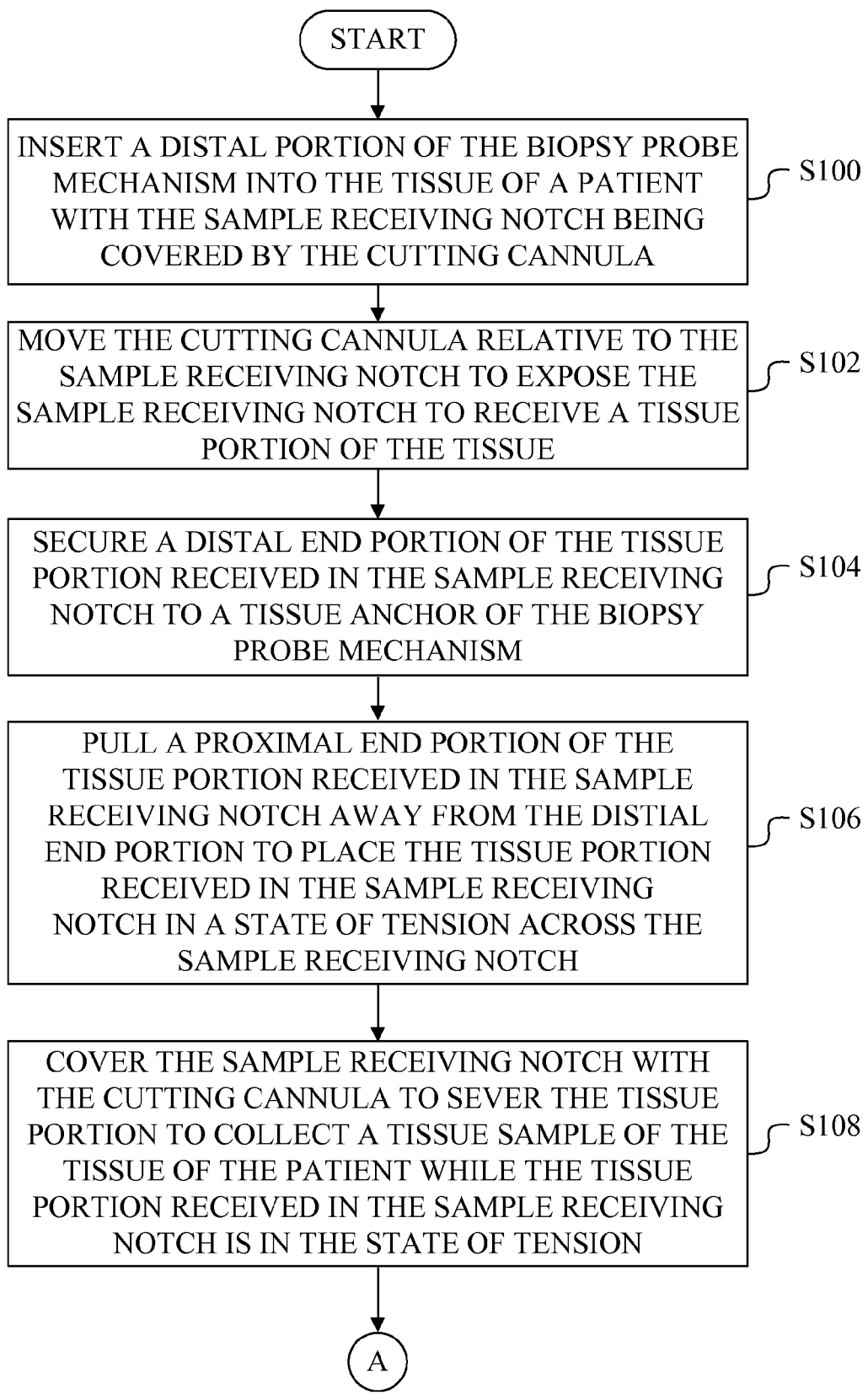
FIGS. 7A and 7B show a flowchart of a method for using the biopsy apparatus of FIG. 1 in the harvesting of a tissue sample.
Figure 7B:
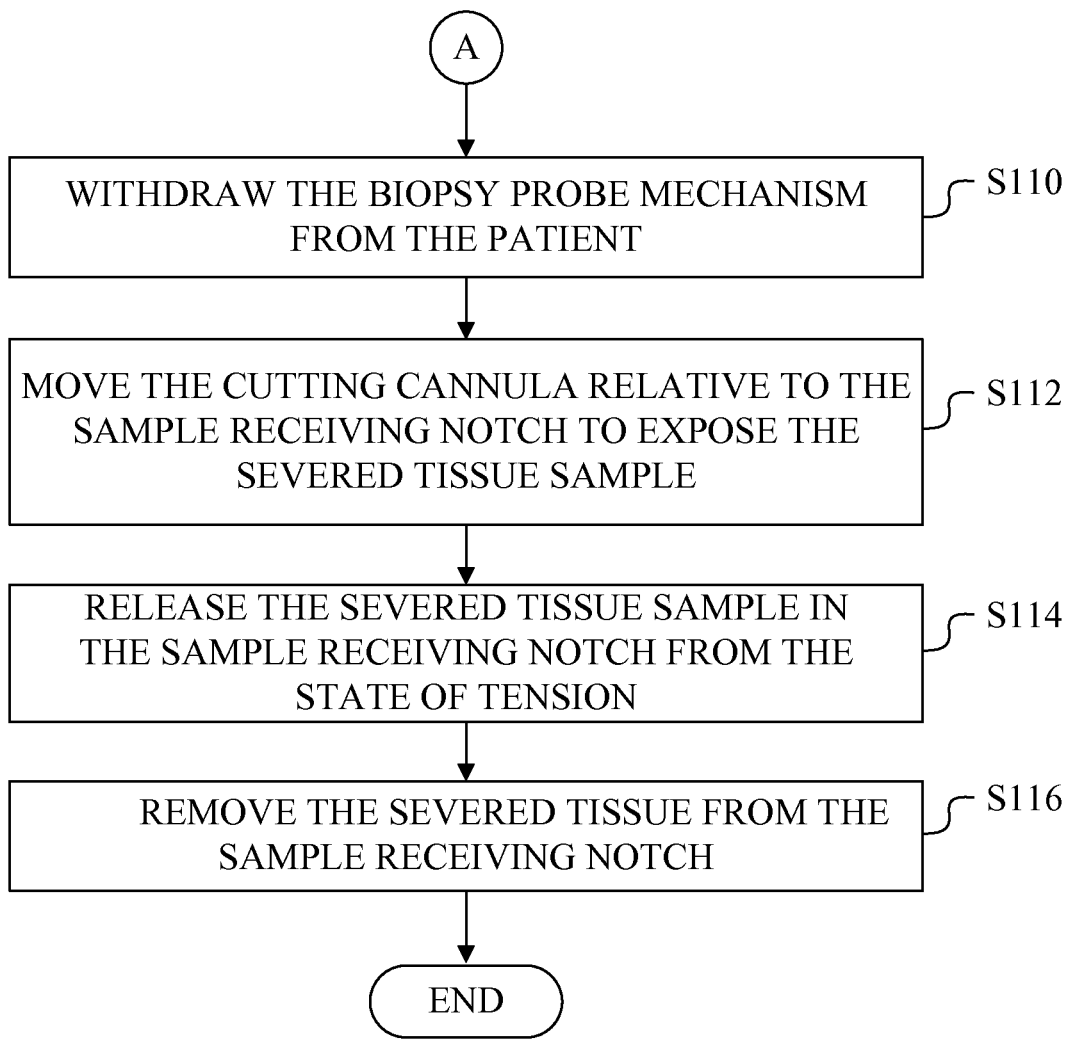

FIGS. 7A and 7B show a flowchart of a method for using biopsy apparatus of FIG. 1. The method of FIGS. 7A and 7B will be described with reference to FIGS. 1 and 8-10, which illustrate a portion of the operational sequence of the operation of biopsy apparatus 10 of FIG. 1 in the harvesting of a tissue sample.

Figure 8:
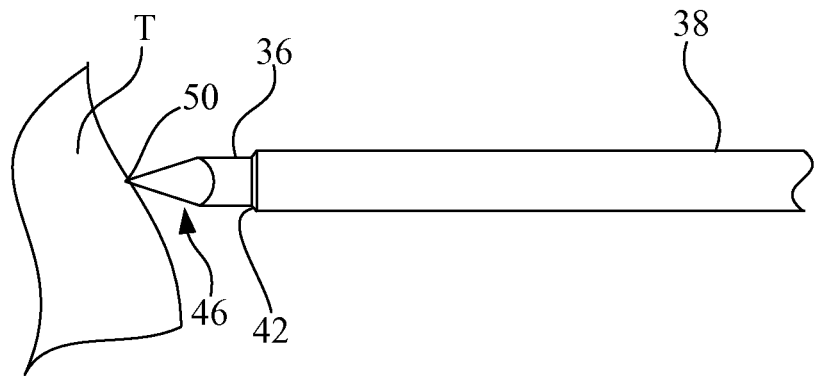
FIGS. 8, 9 and 10 illustrate an operational sequence of the operation of the biopsy apparatus of FIG. 1 in the harvesting of a tissue sample, from a top view perspective of the elongate member of the biopsy probe mechanism of FIG. 1.

At act S100, with reference to FIG. 8, a distal portion of biopsy probe mechanism 14 is inserted into tissue T of a patient with sample receiving notch 54 being covered by cutting cannula 38 until sample receiving notch 54 is positioned adjacent to the tissue to be biopsied.

Figure 9:
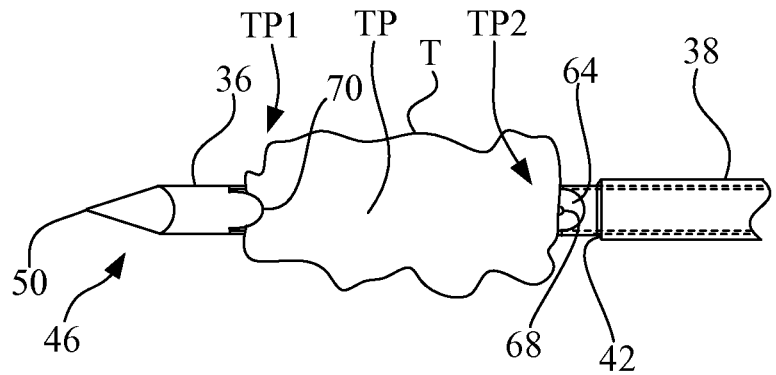

At act S102, with reference to FIG. 9, cutting cannula 38 is moved relative to sample receiving notch 54 to expose sample receiving notch 54 to receive a tissue portion TP of the tissue T to be biopsied. For example, commands may be sent by user interface 20 to electromechanical drive 26 via controller 22 to open sample receiving notch 54 by retracting cutting cannula 38 along longitudinal axis 40, or by advancing sample receiving notch 54.

At act S104, a distal end portion TP1 of the tissue portion TP received in sample receiving notch 54 is secured to a tissue anchor of biopsy probe mechanism 14. The securing is performed, for example, by tissue anchor 70 or alternatively tissue anchor 84, which may be physically moved along longitudinal axis 40 a short distance, e.g., 1 to 5 millimeters, in a reciprocating fashion to engage the tissue T.

At act S106, a proximal end portion TP2 of the tissue portion TP received in sample receiving notch 54 is pulled away from the distal end portion TP1 to place the tissue portion TP received in sample receiving notch 54 in a state of tension across sample receiving notch 54. The pulling of the proximal end portion TP2 of the tissue portion TP may be performed by exposing the proximal end portion TP2 of the tissue portion TP to a vacuum generated by pressure source 28, e.g., via hole 68 at proximal end wall 64 of sample receiving notch 54, to tend to pull the tissue portion TS away from tissue anchor 70 (see FIGS. 1-4), or alternatively tissue anchor 84 (see FIG. 5), across sample receiving notch 54 along longitudinal axis 40. For example, commands may be sent via controller 22 to electromechanical drive 26 to operate pressure source 28 to generate a vacuum so as to selectively draw the tissue portion TP into sample receiving notch 54 and pull tissue portion TP toward hole 68 away from tissue anchor 70, or alternatively tissue anchor 84.

Figure 10:
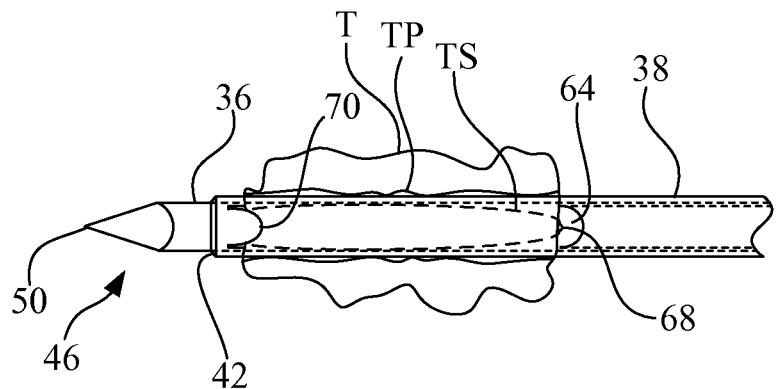

At act S108, with reference to FIG. 10, sample receiving notch 54 is covered with cutting cannula 38 to sever the tissue portion TP to collect a tissue sample TS from the tissue T of the patient while the tissue portion TP received in the sample receiving notch 54 is in the state of tension. For example, commands may be sent by controller 22 to electromechanical drive 26 to extend cutting cannula 38 relative to sample receiving notch 54 along longitudinal axis 40 toward piercing tip 50.

At act S110, the biopsy probe mechanism 14 is withdrawn from patient.

At act S112, cutting cannula 38 is moved relative to sample receiving notch 54 to expose sample receiving notch 54, and thus expose the severed tissue sample TS. For example, commands may be sent by user interface 20 to electromechanical drive 26 via controller 22 to open sample receiving notch 54 by retracting cutting cannula 38 along longitudinal axis 40, or by advancing sample receiving notch 54.

At act S114, the severed tissue sample TS in sample receiving notch 54 is released from the state of tension. The release occurs by turning off the vacuum present at hole 68, e.g., by turning off pressure source 28.

At act S116, the severed tissue sample TS is removed from the sample receiving notch 54. Thus, the tissue sample TS is retained in sample receiving notch 54 of elongate member 36 until physically removed.

It is noted that the sequential order of the process acts set forth above is by example. The order of some of the process acts may be changed from the specific order set forth, or combined as a single act. For example, it is to be understood that the release of the tissue sample from the state of tension may occur at any time after biopsy probe mechanism 14 is withdrawn from the patient. Also, for example, process acts S104 and S106 may be occur in sequence or simultaneously.

In the embodiments described above, using the downwardly facing sharpened tip of tissue anchor 70 or tissue anchor 84 in combination with vacuum provided by pressure source 28 to hold both the distal end TP1 and the proximal end TP2, respectively, of the tissue portion TP and place tissue portion TP in tension during the severing of tissue sample TS results in a tissue sample of increased size and/or quality over that which would be otherwise obtained in the absence of such an arrangement.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device, comprising:
   a vacuum source;
   an elongate member having a proximal end, a distal end, an outer surface, a lumen in fluid communication with said vacuum source, and a longitudinal axis extending between said proximal end and said distal end, said distal end having a piercing tip;
   a sample receiving notch formed in said elongate member, said sample receiving notch defining a side port adjacent said outer surface, said sample receiving notch being configured to extend inwardly from said side port and terminate at a sample floor in an interior of said elongate member, said sample receiving notch having a proximal end wall and a distal end wall, said distal end wall being located between said distal end and said proximal end wall, said proximal end wall being separated from said distal end wall along said longitudinal axis, said floor extending between said proximal end wall and said distal end wall, said proximal end wall having a hole in fluid communication with said lumen; and
   a tissue anchor having a cantilever portion with a free end, said cantilever portion configured to extend from a distal portion of said elongate member adjacent to said sample receiving notch toward said proximal end wall of said sample receiving notch, and having a sharp tip that extends from said free end of said cantilever portion toward said sample floor,
   wherein said sharp tip includes a planar face, and a plane of said planar face is oriented to intersect said sample floor, said planar face oriented to face said distal end wall,
   said tissue anchor and said proximal end wall having said hole collectively configured to place tissue received in said sample receiving notch in a state of tension between said planar face of said tissue anchor and said proximal end wall when a vacuum is applied by said vacuum source to said hole in said proximal end wall.

2. The biopsy device of claim 1, wherein said elongate member is a cylindrical tube, said sample floor is a first portion of a side wall of said cylindrical tube, and said tissue anchor is formed from a second portion of said side wall of said cylindrical tube.

3. The biopsy device of claim 1, wherein said cantilever portion includes a plurality of cantilevered members.

4. The biopsy device of claim 1, wherein said free end of said cantilever portion of said tissue anchor has a head portion having a proximal rounded surface, and with said planar face of said sharp tip being located distal to the proximal rounded surface of said head portion.

5. The biopsy device of claim 1, said tissue anchor comprising a head portion at said free end of said cantilever portion, said head portion configured to extend in a cantilevered manner from said cantilever portion, said head portion configured to define said sharp tip having said planar face.

6. The biopsy device of claim 5, wherein said head portion has a proximal rounded surface, and with said planar face of said sharp tip being located distal to the proximal rounded surface of said head portion.

7. A biopsy probe mechanism, comprising:
   a vacuum source;
   a frame;
   a cutting cannula; and
   an elongate member arranged coaxially with said cutting cannula, said cutting cannula and said elongate member being coupled to said frame, said elongate member having a proximal end, a distal end, an outer surface, and a longitudinal axis extending between said proximal end and said distal end;
   a lumen located in said elongate member, said lumen beginning at said proximal end and extending toward said distal end along said longitudinal axis, said lumen in fluid communication with said vacuum source;

a sample receiving notch formed in said elongate member, said sample receiving notch defining a side port adjacent said outer surface, said sample receiving notch being configured to extend inwardly from said side port and terminate at a sample floor in an interior of said elongate member, said sample receiving notch having a proximal end wall and a distal end wall, said distal end wall being located between said distal end and said proximal end wall, said proximal end wall being separated from said distal end wall along said longitudinal axis, said floor extending between said proximal end wall and said distal end wall, said proximal end wall having a hole that facilitates fluid communication between said sample receiving notch and said lumen; and a tissue anchor having a cantilever portion with a free end, said cantilever portion configured to extend proximally from a distal portion of said elongate member adjacent to said sample receiving notch toward said proximal end wall of said sample receiving notch, and having a sharp tip that extends from said free end of said cantilever portion toward said sample floor, wherein said sharp tip includes a planar face, said planar face oriented to face said distal end wall of said sample receiving notch, said tissue anchor and said proximal end wall having said hole collectively configured to place tissue received in said sample receiving notch in a state of tension between said planar face of said tissue anchor and said proximal end wall when a vacuum is applied by said vacuum source to said hole in said proximal end wall.

8. The biopsy probe mechanism of claim 7, wherein said elongate member is a cylindrical tube, said sample floor is a first portion of a side wall of said cylindrical tube, and said tissue anchor is formed from a second portion of said side wall of said cylindrical tube.

9. The biopsy probe mechanism of claim 7, wherein said sample floor is a portion of a side wall of said elongate member.

10. The biopsy probe mechanism of claim 7, wherein said cantilever portion includes a plurality of cantilevered members.

11. The biopsy probe mechanism of claim 7, said tissue anchor comprising a head portion at said free end of said cantilever portion, said head portion configured to extend in a cantilevered manner from said cantilever portion, said head portion configured to define said sharp tip having said planar face.

12. The biopsy probe mechanism of claim 11, wherein said head portion has a proximal rounded surface, and with said planar face of said sharp tip being located distal to the proximal rounded surface of said head portion.

13. A biopsy apparatus, comprising:

a driver assembly having a housing configured to be grasped by a user;

a pressure source;

a biopsy probe mechanism drivably coupled to said driver assembly, said biopsy probe mechanism including:

a cutting cannula; and an elongate member arranged coaxially with said cutting cannula, said elongate member having a proximal end, a distal end, an outer surface, and a longitudinal axis extending between said proximal end and said distal end;

a lumen located in said elongate member, said lumen beginning at said proximal end and extending toward said distal end along said longitudinal axis, said lumen being connected in fluid communication with said pressure source;

a sample receiving notch formed in said elongate member, said sample receiving notch defining a side port adjacent said outer surface, said sample receiving notch being configured to extend inwardly from said side port and terminate at a sample floor in an interior of said elongate member, said sample receiving notch having a proximal end wall and a distal end wall, said proximal end wall being separated from said distal end wall along said longitudinal axis, said floor extending between said proximal end wall and said distal end wall, said proximal end wall having a hole that facilitates fluid communication between said sample receiving notch and said lumen; and a tissue anchor having a cantilever portion with a free end, said cantilever portion configured to extend from a distal portion of said elongate member adjacent to said sample receiving notch toward said proximal end wall of said sample receiving notch, and having a sharp tip that extends toward said sample floor in a cantilevered manner from said free end of said cantilever portion, wherein said sharp tip includes a planar face, and a plane of said planar face is oriented perpendicular to said longitudinal axis, said tissue anchor and said proximal end wall having said hole collectively configured to place tissue received in said sample receiving notch in a state of tension between said planar face of said tissue anchor and said proximal end wall when a vacuum is applied by said pressure source to said hole in said proximal end wall.

14. The biopsy apparatus of claim 13, wherein said elongate member is a cylindrical tube, said sample floor is a first portion of a side wall of said cylindrical tube, and said tissue anchor is formed from a second portion of said side wall of said cylindrical tube.

15. The biopsy apparatus of claim 13, wherein said sample floor is a portion of a side wall of said elongate member, said longitudinal axis being interposed between said side port and said sample floor.

16. The biopsy apparatus of claim 13, wherein said cantilever portion includes a plurality of cantilevered members.

17. A method for performing a biopsy procedure with a biopsy apparatus having a vacuum source and a biopsy probe mechanism, said biopsy probe mechanism having a cutting cannula, an elongate member having a longitudinal axis, a sample floor, a sample receiving notch, and a lumen in fluid communication with said vacuum source, and a tissue anchor adjacent said sample receiving notch cantilevered over said sample floor, the tissue anchor having a sharp tip that extends toward said sample floor from a free end of said tissue anchor, wherein said sharp tip includes a planar face, and a plane of said planar face is oriented perpendicular to said longitudinal axis, said sample receiving notch having a proximal end wall and a distal end wall, said proximal end wall being separated from said distal end wall along said longitudinal axis, said proximal end wall having a hole in fluid communication with said lumen, comprising:

inserting a distal portion of said biopsy probe mechanism into tissue of a patient with the sample receiving notch being covered by said cutting cannula;

moving said cutting cannula relative to said sample receiving notch to expose the sample receiving notch to receive a tissue portion of said tissue;

securing a distal end portion of said tissue portion received in said sample receiving notch to said tissue anchor with said sharp tip that extends toward said sample floor of said biopsy probe mechanism by engaging said distal end portion of said tissue portion with said sharp tip that extends toward said sample floor from the cantilevered free end of said tissue anchor;

pulling a proximal end portion of said tissue portion received in said sample receiving notch away from said distal end portion such that the tissue portion is engaged by said planar surface of said sharp tip at said free end of said tissue anchor to place said tissue portion received in said sample receiving notch in a state of tension across said sample receiving notch when a vacuum is applied by said vacuum source to said hole in said proximal end wall; and covering said sample receiving notch with said cutting cannula to sever said tissue portion to collect a tissue sample of said tissue of said patient while said tissue portion received in said sample receiving notch is in said state of tension.

18. The method of claim 17, further comprising:

withdrawing said biopsy probe mechanism from said patient;

moving said cutting cannula relative to said sample receiving notch to expose the severed tissue sample;

releasing the severed tissue sample in said sample receiving notch from the state of tension; and removing the severed tissue from the sample receiving notch.

\* \* \* \* \*